(12) United States Patent
Conway et al.

(10) Patent No.: US 6,915,282 B1
(45) Date of Patent: Jul. 5, 2005

(54) AUTONOMOUS DATA MINING

(75) Inventors: Andrew Conway, Stanford, CA (US); Peter Eastman, Belmont, CA (US); Howard Snortland, Menlo Park, CA (US); Barrett Eynon, Menlo Park, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 657 days.

(21) Appl. No.: 09/776,244

(22) Filed: Feb. 2, 2001

Related U.S. Application Data

(60) Provisional application No. 60/243,650, filed on Oct. 26, 2000.

(51) Int. Cl.[7] .................................................. G06N 5/00
(52) U.S. Cl. ............................................. 706/12; 707/6
(58) Field of Search ............................ 706/12, 13, 45, 706/48, 50; 707/6, 1

(56) References Cited

U.S. PATENT DOCUMENTS

| | | | |
|---|---|---|---|
| 5,732,218 A | 3/1998 | Bland et al. ................. | 709/224 |
| 5,892,909 A | 4/1999 | Grasso et al. ................ | 709/201 |
| 5,933,818 A | 8/1999 | Kasravi et al. .............. | 706/12 |
| 6,012,058 A | 1/2000 | Fayyad et al. ................. | 707/6 |
| 6,073,138 A | 6/2000 | De l'Etraz et al. ......... | 707/104.1 |
| 6,112,194 A | 8/2000 | Bigus .......................... | 706/11 |
| 6,115,708 A | 9/2000 | Fayyad et al. ................. | 707/6 |
| 6,151,584 A | 11/2000 | Papierniak et al. ........... | 705/10 |
| 6,151,601 A | 11/2000 | Papierniak et al. ........... | 707/10 |
| 6,185,561 B1 * | 2/2001 | Balaban et al. ................ | 707/6 |
| 6,687,692 B1 * | 2/2004 | Balaban et al. ................ | 707/6 |
| 2002/0087275 A1 * | 7/2002 | Kim et al. .................... | 702/19 |
| 2003/0097222 A1 * | 5/2003 | Craford et al. ............... | 702/20 |
| 2003/0172043 A1 * | 9/2003 | Guyon et al. ................. | 706/48 |

OTHER PUBLICATIONS

Scherf et al., "A Gene Expression Database For The Molecular Pharmacology of Cancer", Nature Genetics, Mar. 1, 2000, Vo 24, No. 3, pp. 236–244.*

* cited by examiner

Primary Examiner—Wilbert L. Starks, Jr.

(57) ABSTRACT

The invention provides a method and system for performing data mining autonomously with regard to a set of data, and formulating hypotheses in response thereto. An autonomous software element (a) collects sets of data, along with collateral data, into a unified extensible database; (b) formulates possibly interesting hypotheses with regard to those data; (c) evaluates hypotheses, thus relating each hypothesis against a probability it could have occurred by chance; (d) rates each hypothesis in response to multiple factors; (e) reports those hypotheses to users, selecting those users who are most likely to be interested and who are most interested in being informed.

35 Claims, 3 Drawing Sheets

215(c)
If the statistical tests indicate that the hypothesis evaluation module 113 can confidently reject the possibility that the hypothesis was true by chance, the hypothesis is marked as publishable and possibly "interesting."

216
The publication module 115 generates a publication regarding the publishable hypothesis. The publication can include a database or other data file in a specified format, an HTML (hypertext markup language) page, or an email message.

220
The autonomous software element 110 has completed one cycle of finding and publishing a publishable hypothesis. The method 200 continues with the flow point 210, unless interrupted by the operator 117.

FIG. 2B

AUTONOMOUS DATA MINING

This application claims the benefit of Provisional Application No. 60/243,650, filed Oct. 26, 2000.

This invention was made with government support under Small Business Innovation Research Grant/Contract Number 2R44HG10894-02, awarded by the National Institutes of Health. The Government has certain rights in the invention.

BACKGROUND OF THE INVENTION

1. Field of the Invention

This invention relates to autonomous data mining, such as for example autonomous data mining in large sets of gene expression data.

2. Related Art

In computer systems having relatively large amounts of data, such as recorded in a database system or other system for storage and retrieval of data, it is sometimes desirable to review that data to find if there are relationships between data elements that were previously unconfirmed or even unknown. This process is sometimes called "data mining," and is typically applied to programmed processes that are applied to relatively large databases. For example, searching a large database of stock data for those securities that meet predetermined criteria for capitalization and earnings would be a form of data mining.

Known methods of data mining include "clustering," that is, attempting to divide the multiple data elements into a relatively small set of clusters. Other known methods include applying statistical methods to best-fit a predetermined relationship against the set of data, so as to determine a set of parameters for the predetermined relationship. These other known methods include multiple linear regression and other statistical and stochastic techniques. While these methods of the known art can generally achieve the purpose of evaluating predetermined relationships against a relatively large set of data, they are of course subject to the drawbacks of all statistical methods, which is that they can only deliver a probabilistic assessment of the predetermined relationship against the set of data.

One problem with the known art is that the researcher or other person (that is, a "user") must have a predetermined relationship in mind before attempting to apply it against the set of data. For example, when searching a large database of stock data, the user must have a predetermined relationship and a set of predetermined stock parameters in mind for evaluation before known data mining techniques can evaluate whether that predetermined relationship applies well to that set of predetermined stock parameters. This could be referred to as a hypothesis-generating problem.

A second problem with the known art is that the predetermined relationship might have little or no relationship to domain-specific knowledge about the set of data. For example, when searching a large database of stock data, the user might request evaluation of a predetermined relationship among a set of predetermined stock parameters that have, in any real-world model of the stock market, no relationship to each other (such as, for example, whether stocks with a price/earnings ratio that is a prime number occur more frequently when the Moon is in the Aries constellation). This could be referred to as the uninteresting-hypothesis problem.

A third problem with the known art is that the predetermined relationship and the set of data must be determined ahead of the operation of the data mining method. For example, when searching a large database of stock data, the user must assure that all needed data is available before attempting to perform data mining. This could be referred to as the known-database problem.

All three of these problems are particularly acute in the field of scientific research into gene expression.

First, databases of gene expression data have been collected by researchers and are often made available to each other, either in the context of academic research or in the context of pharmaceutical or other for-profit research and development. These databases are relatively large, and are getting substantially larger as time goes by, both due to work by researchers in obtaining new gene expression data and due to improved methods for obtaining that data in greater quantity and at greater speed. As an emergent consequence of the rapid growth of databases of gene expression data, it has become extremely difficult for individual researchers to maintain familiarity even with the scope of data available for review.

Second, gene expression data includes raw data describing measurements of activity for individual strands of mRNA (messenger RNA). These measurements can differ in response to differing times they were taken, differing patients they were taken from, differing clinical samples from one or more patients, differing medical conditions of the one or more patients, differing prescription or other drugs the patients were under the influence of, differing chemical milieus in which the measurements were taken, and many other possible differing conditions. Collection, recording and publication of gene expression data are known in the art of biochemical research. As might be inferred from this description, sets of gene expression data can be extremely complex, having no immediate relationships available to the reviewer of the data. Moreover, new sets of gene expression data are generated from time to time, thus increasing the available pool of gene expression data relatively continuously.

Third, the research community does not always make these sets of gene expression data available immediately upon production. Sometimes individual sets of data are checked for consistency or quality control. Sometimes one or more researchers have a particular predetermined relationship they would like to evaluate (and publish) before allowing other research groups to access those sets of data. As the number and size of sets of gene expression data becomes larger, and as the number of researchers interested in those sets of data becomes larger, the chance that a valuable set of data is not available to one or more researchers interested in that valuable set of data becomes greater.

Fourth, the particular biological processes that sets of gene expression data reflect are relatively complex. There are relatively large numbers of genes, activation of each of which possibly affects large subsets of other genes, in ways that are presently not well known. (That is why study of gene expression data is called "research.") Many of these processes are highly nonlinear, that is, a small change in amount of gene expression for a first gene can result in very large changes in amounts of gene expression for one or more downstream sets of genes. Many of these processes have feedback, feed-forward, or other complex topological loops, so that gene expression for a first gene can have multiple different effects on gene expression for both a second gene and for the first gene itself. Even relatively simple examples known as cell cycles can involve relatively long feedback loops, each element of which itself includes a relatively complex set of interactions.

Known methods of examining gene expression data include examining the data "by hand," that is, by an interested researcher who formulates hypotheses, performs operations on the data to evaluate those hypotheses, and determines if there is sufficient support for those hypotheses to warrant further experiment or even publication of results of the evaluation. While these known methods generally achieve the goals of finding and publishing interesting and useful statements about gene expression to the research world, they are subject to several drawbacks. As noted above, there is a relatively large amount of gene expression data. The amount of such data is rapidly increasing and is not easily subject to efficient or effective search by human researchers. Researchers do not have adequate time to review all the relevant data. Researchers also do not have adequate time to determine all the relevant data in their field, or in related fields. Researchers also often work in close-knit groups and are therefore not always aware of similar work being performed by other researchers. Moreover, as noted above, problems in gene expression analysis are relatively complex, and are therefore not easily subject to "by hand" analysis of extensive data.

Accordingly, it would be desirable to provide a technique in which data mining is performed with regard to a set of data, possibly interesting hypotheses are formulated in response thereto, and those hypotheses are reported. In one aspect of the invention, this technique can be achieved by performing a robotic process with regard to a set of data in a database, so as to formulate potentially interesting hypotheses and so as to communicate those hypotheses to researchers and other persons having an interest therein.

SUMMARY OF THE INVENTION

The invention provides a method and system for performing data mining autonomously with regard to a set of data, and formulating hypotheses in response thereto. An autonomous software element collects sets of data (such as gene expression data), along with collateral data (such as information about published papers, individual researchers, and known relationships between genes), into a unified but extensible database. The autonomous software element formulates possibly interesting hypotheses with regard to data findable in the database. The autonomous software element evaluates each such possibly interesting hypothesis against the data in the database, providing a result that relates the possibly interesting hypothesis against a probability it could have occurred by chance. The autonomous software element rates each possibly interesting hypothesis, in response to multiple factors, such as for example (1) if they relate to genes one or more researchers have indicated they are interested in, (2) if they relate to genes for which there are published papers, (3) if they are relatively simple and relatively unlikely to be due to chance, (4) if they are relatively consistent or relatively inconsistent with domain-specific knowledge about known effects of gene expression. The autonomous software element reports those hypotheses to researchers and other interested persons (collectively, "users"), selecting those users who are most likely to be interested in each specific hypothesis and who are most interested in being informed of such discoveries.

As an emergent consequence of the invention, autonomous data mining of a database including a set of data (such as for example a set of gene expression data) produces a set of possibly interesting hypotheses, each of which can itself be graded with regard to a set of selected parameters. Additional data, such as research interests, published papers, and the like, can provide information for grading the hypotheses and for grading communications to researchers. The set of hypotheses and additional data itself provides a database for use in determining which hypotheses to report to which researchers and which other persons. This has the advantages of allowing (1) reporting of interesting hypotheses to those researchers most likely to take action thereon, and (2) filtering of which hypotheses to report in response to researcher preferences.

The invention provides an enabling technology for a wide variety of applications for data mining and hypothesis testing, to obtain substantial advantages and capabilities that are novel and non-obvious in view of the known art.

BRIEF DESCRIPTION OF THE DRAWINGS

FIGS. 2A and 2B show a flow diagram of a method of operating a system as in FIG. 1.

DETAILED DESCRIPTION OF THE PREFERRED EMBODIMENT

In the following description, a preferred embodiment of the invention is described with regard to preferred process steps and data structures. Embodiments of the invention can be implemented using general-purpose processors or special purpose processors operating under program control, or other circuits, adapted to particular process steps and data structures described herein. Implementation of the process steps and data structures described herein would not require undue experimentation or further invention.

Related Applications

Inventions described herein can be used in conjunction with inventions described in the following document(s).

U.S. Provisional Patent Application Ser. No. 60/243,650, filed Oct. 26, 2000, in the name of the same inventor, titled "Enterprise-wide Data Mining."

Each of these documents is hereby incorporated by reference as if fully set forth herein. This application claims priority of each of these documents. These documents are collectively referred to as the "Incorporated Disclosures."

System Elements

Figure 1:
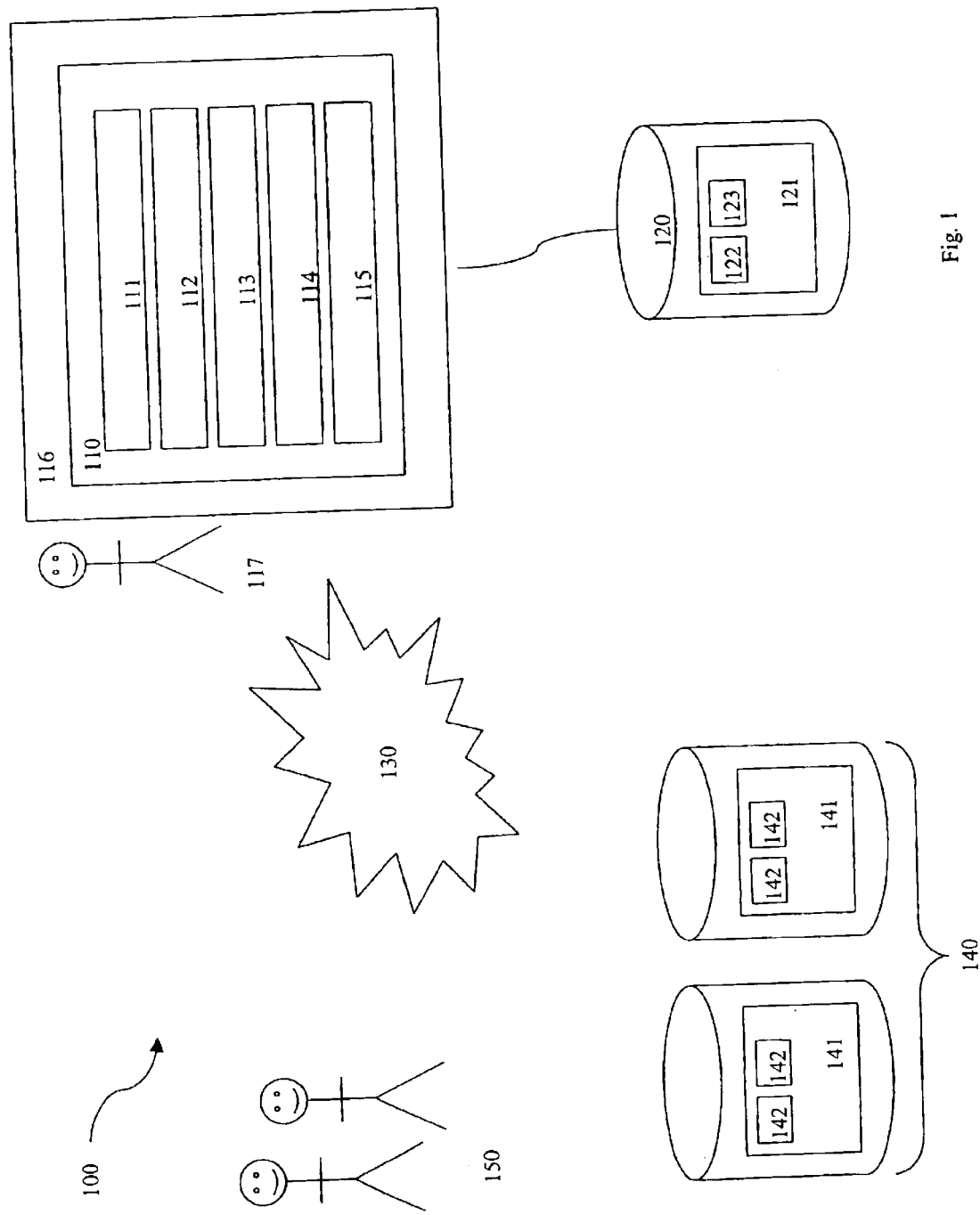
FIG. 1 shows a block diagram of a system used with an autonomous data mining tool.

FIG. 1 shows a block diagram of a system used with an autonomous data mining tool.

A system 100 includes an autonomous software element 110, a local database 120, a communication link 130, a set of external databases 140, and a set of users 150.

The autonomous software element 110 includes a database access module 111, a hypothesis formulation module 112, a hypothesis evaluation module 113, an interest-matching module 114, and a publication module 115.

In a preferred embodiment, the autonomous software element 110 is disposed for execution as an application program under control of operating system software on any general-purpose computer workstations 116, such as a PC, Macintosh, or another type of workstation. The workstation has a processor, program and data memory, mass storage, an input device, and a display device. The workstation 116 can run without supervision, or can be controlled by an operator 117. Computer workstations are known in the art of computing. The workstation 116 may include a general-purpose computer workstation, a laptop computer, a handheld or "palmtop" computer, or another type of communication or computing device. Due to the computational and memory requirements of the preferred embodiment, the workstation 116 preferably includes substantial processor, memory and mass storage resources. In other embodiments, the workstation 116 may include a plurality of workstations, so as to share memory and other computational resources.

In a preferred embodiment, each operator 117 includes one or more human operators of an individual workstation 116. However, in alternative embodiments, one or more operators 117 may include a proxy, such as an artificial intelligence program, a database-querying program, a web-browsing program, some other form of interface program to one or more actual human beings or other quasi-intelligent devices, or other control programs capable of generating requests for information or responding to responses to those requests.

The database access module 111 includes executable software disposed for execution by the workstation 116, and responsive to commands from the operator 117, capable of communication with the local database 120. The database access module 111 communicates with the local database 120 by sending database requests, and receiving database responses, from the local database 120. The database access module 111 obtains sets of gene expression data from the local database 120, records them in data memory for the workstation 116, and provides those sets of gene expression data to the hypothesis formulation module 112, the hypothesis evaluation module 113, the interest-matching module 114, and the publication module 115.

The hypothesis formulation module 112 includes executable software disposed for execution by the workstation 116, and responsive to commands from the operator 117, capable of receiving gene expression data and operating on that gene expression data (as further described below) so as to generate a set of hypotheses.

The hypothesis evaluation module 113 includes executable software disposed for execution by the workstation 116, and responsive to commands from the operator 117, capable of receiving a set of hypotheses from the hypothesis formulation module 112, and capable of evaluating those hypotheses (as further described below) for relative interest and likelihood.

The interest-matching module 114 includes executable software disposed for execution by the workstation 116, and responsive to commands from the operator 117, capable of receiving a set of hypotheses from the hypothesis evaluation module 113, and capable of matching those hypotheses (as further described below) with a set of data regarding users, so as to evaluate which users are most likely to be interested in those hypotheses, and so as to evaluate which users are most likely to want to be informed thereof.

The publication module 115 includes executable software disposed for execution by the workstation 116, and responsive to commands from the operator 117, capable of receiving a set of hypotheses and a set of corresponding users from the interest-matching module 114, and capable of publishing those hypotheses to those users. In a preferred embodiment, the publication module 115 generates an email message for each such hypothesis to each such user, and sends that email message using the communication link 130 to the target user.

The local database 120 includes a database system 121, having a set of gene expression data elements 122 and a set of collateral data elements 123 recorded therein.

The database system 121 is accessible to the autonomous software element 110 by relatively local techniques. In a preferred embodiment, the local database 120 is coupled directly to the workstation 116. In alternative embodiments, the local database 120 may be accessible to the workstation 116 using a LAN (local area network), using the communication link 130, or using any other technique by which the autonomous software element 110 can relatively rapidly and reliably access relatively large amounts of data recorded in the local database 120. In a preferred embodiment, the local database 120 includes a standard relational or object-oriented database system, such as the "Oracle" product available from Oracle Corporation of Redwood City, Calif.

The gene expression data elements 122 each include information regarding a particular gene expression measurement, including information regarding times they were taken, patients they were taken from, clinical samples from one or more patients, medical conditions of the one or more patients, prescription or other drugs the patients were under the influence of, the chemical milieu in which the measurements were taken, and other relevant conditions.

The collateral data elements 123 each include information such as the following:

information regarding particular genes, possibly including information regarding known or hypothesized interactions with other genes, gene-sequence data and organism sequence data.

particular researchers, possibly including information regarding (1) individual genes or gene expressions those researchers have particular interest in, (2) the degree of receptivity to messages from the autonomous software element those researchers have;

published results and/or papers, possibly including (1) further domain-specific knowledge regarding individual genes or gene expressions, (2) known relationships between individual researchers, such as having collaborated on papers together or being located at the same or related institutions.

The communication link 130 includes a physical communication link, control software, and communication protocols for devices attached thereto to send and receive messages. The communication link 130 can include an internet, intranet, extranet, VPN (virtual private network), private or public switched network, ATM network, LAN (local area network), WAN (wide area network), direct communication line, shared memory communication, or any other technique capable of performing the functions described herein. In a preferred embodiment, the communication link 130 includes an internet and a LAN connection to the internet.

The external databases 140, similar to the local database 120, include database systems 141, each having a set of data elements 142 recorded therein.

The database systems 141 are accessible to the autonomous software element 110 using the communication link 130. The external databases 140 may include standard relational or object-oriented database systems, or may include text files or other data formats readable by the autonomous software element 110 (including HTML).

The gene expression data elements 142 in the external databases 140 include sets of gene expression data. In a preferred embodiment, gene expression data elements 142 include elements similar to the gene expression data elements 122.

The collateral data elements 143 in the external databases 140 include information regarding published papers, individual researchers, and known relationships between genes. In a preferred embodiment, collateral data elements 143 include elements similar to the collateral data elements 123.

The users 150 each include researchers, other interested persons, or interested groups or institutions, each having a workstation 116 and an operator 117, similar to the autonomous software element 110.

Method of Operation

Figure 2A:
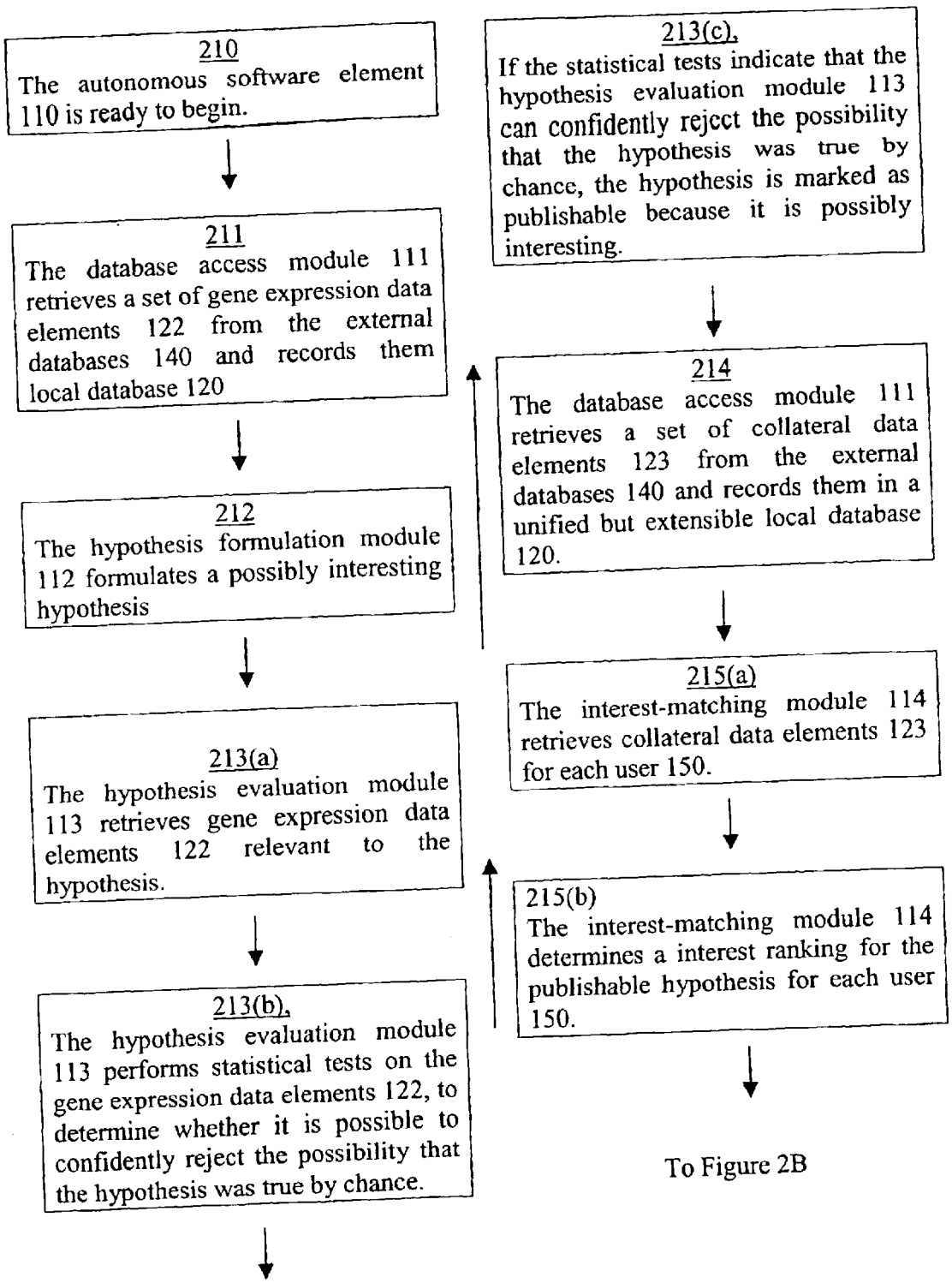

FIGS. 2A and 2B show a flow diagram of a method of operating a system as in FIG. 1.

A method 200 includes a set of flow points and process steps as described herein.

Although by the nature of textual description, the flow points and process steps are described sequentially, there is no particular requirement that the flow points or process steps must be sequential. Rather, in various embodiments of the invention, the described flow points and process steps can be performed in a parallel or pipelined manner, either by one device performing multitasking or multithreading, or by a plurality of devices operating in a cooperative manner. Parallel and pipelined operations are known in the art of computer science.

At a flow point 210, the autonomous software element 110 is ready to begin.

At a step 211, the database access module 111 retrieves a set of gene expression data elements 122 from the external databases 140 and records them in a unified but extensible local database 120. In a preferred embodiment, the database access module 111 operates from time to time to re-perform this step, even if other parts of the autonomous software element 110 are operating in parallel.

At a step 212, the hypothesis formulation module 112 formulates a possibly interesting hypothesis. To perform this step, the hypothesis formulation module 112 does one or more of the following:

Comparing sets of genes: The hypothesis formulation module 112 identifies a test set $G_T$ of genes, as follows: (1) The hypothesis formulation module 112 prepares a set of genes $G_C$ found by clustering, as further described below. (2) The hypothesis formulation module 112 compares the set of genes $G_C$ found by clustering with other known sets of genes $G_K$ found by other means. For example, known sets of genes $G_K$ found by other means can include genes found by matching keywords in the external databases 140, or other private or public databases. (3) The hypothesis formulation module 112 performs a statistical technique to determine a probability of overlap between the clustering set $G_C$ and the known set $G_K$. If the statistical technique indicates that the probability is relatively low, the hypothesis formulation module 112 concludes that the clustering list $G_C$ would be a useful test set $G_T$.

Comparing upstream sequences: (1) The hypothesis formulation module 112 prepares a set of genes $G_C$ found by clustering, using a clustering technique as further described for "Comparing sets of genes." (2) The hypothesis formulation module 112 gathers from database 120 sequences of nucleotides upstream from the genes in the clustering set $G_C$. (3) The hypothesis formulation module 112 determines if there are relatively short, such as 5–20 bases, sequences that are more common upstream of the clustering set $G_C$ than of other genes in the genome. This could be an interesting observation as it could indicate that these sequences may be regulatory elements for a set of co-regulated genes.

Quality control/data collection: (1) The hypothesis formulation module 112 examines those gene expression data elements 122 from pairs of similar experiments, to determine if their data was poorly collected, taking into account the technology used. For example, for 2 color experiments, hypothesis formulation module 112 checks whether genes with high expression in one experiment tend to be significantly over-expressed or under expressed in the other experiment.

Quality control /experiment replication: (1) The hypothesis formulation module 112 examines those gene expression data elements 122 from replicated experiments, that is, the same experiment performed at differing times. (2) The hypothesis formulation module 112 determines if there is any statistically significant difference between the replicated experiments. For example, the hypothesis formulation module 112 can compute if the number of genes for each experiment that contain extreme values indicates that the numbers are unevenly distributed. A low probability indicates a possibility that data has been incorrectly measured or entered Pathway completion: (1) The hypothesis formulation module 112 examines "pathways" of genes, such that one or more genes, in turn activates the next. A pathway can be represented visually as a network of genes with relationships defined between the genes either of connectedness or physical layout in a 1D, 2D or higher dimensional graph. (2) The hypothesis formulation module 112 looks for sets of genes $G_C$ that might fit into gaps in the pathway, such as by examining each possible gene for each gap in response to (a) a distance metric of expression values for the possible gene and the genes known to be on the pathway, or (b) a distance metric of physical distance for the possible gene and the genes known to be on the pathway. If the relative distances between genes determined with respect to expression data are similar in pattern to the relative distances between genes determined with respect to the pathway diagram, then that gene may fit in that place on the diagram. This is useful as it can place previously unknown genes on a pathway.

Parameter variation: The hypothesis formulation module 112 looks for genes that behave one way in some experiments, and a different way in similar experiments varying only by one or a few parameters. Statistically validation of this can be achieved by estimating experimental error for each point based upon replicates and the absolute expression values.

Unusual behavior: The hypothesis formulation module 112 looks for genes that behave similarly in most experiments, but significantly differently in a few experiments. This is achieved by looking at correlation values in the different experiments, and building a model for the correlations of different genes. If this correlation is significantly different in a small number of experiments, this will be considered important.

Recent data: The hypothesis formulation module 112 looks for experiments or annotations that have been recently added to the local database 120.

As part of this step, the "Comparing sets of genes" and "Comparing upstream sequences" techniques (and possibly also the "Parameter variation" and "Unusual behavior" techniques) use clustering to select a set of genes $G_C$. There are several known techniques for clustering known in the art of data mining.

To perform clustering, the hypothesis formulation module 112 selects a set $E_C$ of gene expression data elements 122 on which to perform clustering. In a preferred embodiment, the set of gene expression data elements 122 is responsive to a common set of information. For example, the common set of information can be one or more of: (1) the gene expression data elements 122 all relate to the same patient, the same drug test, or the same chemical environment; (2) the gene expression data elements 122 all relate to the same keyword; (3) the gene expression data elements 122 all relate to the same researcher or the same time period; (4) the gene expression data elements 122 all relate to interaction of the same first gene $G_1$ with a set of other genes.

In a preferred embodiment, the clustering technique uses hierarchical clustering using nested subtrees of partitions. This is a known technique in the art of statistics.

In alternative embodiments, the clustering technique may include k-means clustering (this technique in known in the art of statistics). In k-means clustering, the set $E_C$ of gene expression data elements 122 is divided into a pre-selected number of clusters $E_1, E_2, \ldots E_N$. Each cluster has a cluster center, initially chosen at random. Each one of the gene expression data elements 122 is assigned to one of the clusters in response to its distance from the cluster center (the one with minimum "distance," according to a selected distance metric). Cluster centers are moved in response to those records assigned to each cluster. This process is repeated until the cluster centers are static to a selected degree.

In other alternative embodiments, the clustering technique may include any other effective clustering technique, such as the following: self-organized maps or user-directed clustering "by hand."

At a step 213, the hypothesis evaluation module 113 tests the hypothesis. To perform this step, the hypothesis evaluation module 113 performs the following substeps:

At a sub-step 213(a), the hypothesis evaluation module 113 retrieves gene expression data elements 122 relevant to the hypothesis.

At a sub-step 213(b), the hypothesis evaluation module 113 performs statistical tests on the gene expression data elements 122, to determine whether it is possible to confidently reject the possibility that the hypothesis was true by chance.

At a substep 213(c), if the statistical tests indicate that the hypothesis evaluation module 113 can confidently reject the possibility that the hypothesis was true by chance, the hypothesis is marked as publishable because it is possibly interesting.

At a step 214, the database access module 111 retrieves a set of collateral data elements 123 from the external databases 140 and records them in a unified but extensible local database 120. In a preferred embodiment, the database access module 111 operates from time to time to re-perform this step, even if other parts of the autonomous software element 110 are operating in parallel.

At a step 215, the interest-matching module 114 compares the publishable hypothesis with collateral data elements 123, so as to determine to which users 150 to publish the publishable hypothesis. In a preferred embodiment, this step is performed in parallel or asynchronously with the other steps of the method 200, as it is possible for a user 150 to change their interests while the autonomous software element 110 is in operation. To perform this step, the interest-matching module 114 performs the following sub-steps:

At a sub-step 215(a), the interest-matching module 114 retrieves collateral data elements 123 for each user 150.

At a sub-step 215(b), the interest-matching module 114 determines a interest ranking for the publishable hypothesis for each user 150. In a preferred embodiment, the interest ranking is responsive to (1) expressions of interest or disinterest by each user 150, (2) general factors tending to indicate interest or disinterest by all users 150, and (3) reliability of data underlying the publishable hypothesis. These collectively include the following factors, amongst others:

whether the user 150 expressed an interest in one of the experiments, genes or gene lists in the publishable hypothesis;

whether the user 150 was an author of a paper, or a provider of data for, any part of the publishable hypothesis;

whether the user 150 expressed an interest in any key word associated with one of the experiments, genes or gene lists in the publishable hypothesis;

whether the user 150 expressed an interest in a "type" of hypothesis;

whether the user 150 expressed an interest in any author of a paper, or a provider of data for, any part of the publishable hypothesis;

whether the user 150 expressed an interest in the genome the genes or gene lists are part of, for the genes or gene lists in the publishable hypothesis;

a measure of age of the gene expression data elements 122 used to form or test the publishable hypothesis;

a measure of time since the gene expression data elements 122 used to form or test the publishable hypothesis were themselves published;

a measure of time since the result was generated by the system modules 112 and 113;

a measure of a number of users 150 who are considered to be interested in the publishable hypothesis or to whom the hypothesis has already been sent;

a measure of a number of users 150 who have responded with feedback regarding whether they were interested in the publishable hypothesis;

a measure of similarity between the publishable hypothesis and other hypotheses other users 150 have considered interesting;

a measure of how many publishable hypotheses, or other knowledge, already exist regarding the genes or gene lists in the publishable hypothesis.

At a sub-step 215(c), if the statistical tests indicate that the hypothesis evaluation module 113 can confidently reject the possibility that the hypothesis was true by chance, the hypothesis is marked as publishable and possibly "interesting."

At a step 216, the publication module 115 generates a publication regarding the publishable hypothesis. The publication can include a database or other data file in a specified format, an HTML (hypertext markup language) page, or an email message. In a preferred embodiment, the publication module 115 generates an HTML page including the largest portion of information associated with the publishable hypothesis, and sends an email message with a synopsis (including a pointer to that HTML page) to each interested user 150.

At a flow point 220, the autonomous software element 110 has completed one cycle of finding and publishing a publishable hypothesis. The method 200 continues with the flow point 210, unless interrupted by the operator 117.

Generality of the Invention

The invention has general applicability to various fields of use, not necessarily related to the particular data, databases, data sets, or uses described above. For example, these fields of use can include one or more of, or some combination of, the following:

experimental data or processes in scientific fields other than biochemistry, such as flow dynamics, materials science, radiochemistry, weather, and experimental data or processes in non-"scientific" fields, such as financial instruments, operations research, product marketing, risk analysis.

Other and further applications of the invention in its most general form, will be clear to those skilled in the art after perusal of this application, and are within the scope and spirit of the invention. Although preferred embodiments are disclosed herein, many variations are possible which remain within the concept, scope, and spirit of the invention, and these variations would become clear to those skilled in the art after perusal of this application.

Technical Appendix

This application includes a technical appendix, hereby incorporated by reference as if fully set forth herein. The technical appendix includes the following:

an example report generated and published by the automated software element.

Although the technical appendix relates to a particular preferred embodiment of the invention, the information in the technical appendix is also applicable to alternative embodiments of the invention, and should be read to indicate the possible scope and spirit of the invention. The technical appendix is not intended to be limiting of the scope or spirit of the invention in any way.

What is claimed is:

1. A method including
   accessing information about a plurality of gene expression values;
   generating from said information a hypothesized relationship about genes relative to said information from a relationship between one or more sets of said gene expression values, said hypothesized relationship having a likelihood of being due to chance not exceeding a predetermined value;
   retrieving data regarding interests of each agent of a plurality of agents;
   identifying at least one agent of the plurality of agents such that the data regarding interests of said at least one agent satisfies at least one predetermined test indicating that said at least one agent has a potential interest in the hypothesized relationship; and
   sending information about said hypothesized relationship to said at least one agent.

2. A method as in claim 1, including collecting said information about the plurality of gene expression values from a plurality of external databases.

3. A method as in claim 1, including collecting said information from at least one external database.

4. A method as in claim 1, wherein generating includes
   selecting a first set of genes in response to said gene expression values;
   selecting a second set of genes in response to data other than said gene expression values;
   applying a statistical technique to said first set and said second set; and
   confirming said hypothesized relationship in response to applying said statistical technique.

5. A method as in claim 1, wherein generating includes
   selecting a set of genes in response to said gene expression values;
   comparing the frequencies of the nucleotide sequences upstream from said set of genes to the frequencies of the nucleotide sequences upstream of genes not in said set; and
   constructing a hypothesis that is responsive to sequences that have an anomalous frequency distribution.

6. A method as in claim 1, wherein generating includes
   examining pathways of genes with respect to gene activation sequences;
   extending said pathways using said gene expression information; and
   constructing a hypothesized relationship concerning an extension of at least one of said pathways.

7. A method as in claim 1, wherein generating includes
   evaluating correlation values with respect to an identified gene or gene sequence so as to determine variations in the behavior of said identified gene or gene sequence; and
   confirming said hypothesized relationship by applying a statistical technique.

8. A method as in claim 1, wherein the step of identifying includes:
   rating said hypothesized relationship with a measure of interest by said at least one agent; and
   selecting said at least one agent responsive to said measure.

9. A method as in claim 8, wherein the step of selecting includes:
   determining a threshold in said measure of interest; and
   comparing said threshold and said measure of interest.

10. A method as in claim 8, wherein said measure of interest is periodically reevaluated.

11. A method as in claim 8, wherein said measure of interest is responsive to complexity of said hypothesized relationship, the likelihood of said hypothesized relationship being due to chance, or whether said hypothesized relationship relates to at least one of: genes one or more researchers have indicated they are interested in, genes for which there are published papers, selected domain-specific knowledge about gene expression.

12. A method as in claim 1, wherein said data regarding interests includes at least one of: information about interests of said at least one agent, information about published papers, information about researchers, information about relationships between genes.

13. Apparatus including
   memory recording information about a plurality of gene expression values;
   an autonomous software element disposed on a computing device, said autonomous software element having access to said memory;
   said memory recording information about a hypothesized relationship between said gene expression values, said hypothesized relationship having the properties of (1) having a likelihood of being due to chance not exceeding a predetermined value, and (2) satisfying at least one predetermined test indicating that said hypothesized relationship is of potential interest to at least one agent; and
   a communication link coupled to said memory and capable of sending information about said hypothesized relationship to said at least one agent.

14. Apparatus as in claim 13, wherein said communication link is capable of collecting said information about the plurality of gene expression values from a plurality of external databases.

15. Apparatus as in claim 13, wherein said communication link is capable of collecting said information from at least one external database.

16. Apparatus as in claim 13, wherein
   said hypothesized relationship includes (a) information about a first set of genes, said first set of genes having been selected in response to said gene expression values, and (b) information about a second set of genes, said second set of genes having been selected in response to data other than said gene expression values;

said hypothesized relationship has been confirmed in response to a statistical technique applied to said first set and said second set.

17. An apparatus as in claim 13, including
a means for selecting a first set of genes in response to said gene expression values;
a means for selecting a second set of genes in response to data other than said gene expression values;
a means for applying a statistical technique to said first set and said second set; and
a means for confirming said hypothesized relationship in response to applying said statistical technique.

18. An apparatus as in claim 13, including
a means for selecting a set of genes in response to said gene expression values;
a means for comparing the frequencies of the nucleotide sequences upstream from said set of genes to the frequencies of the nucleotide sequences upstream of genes not in said set; and
a means for constructing a hypothesis that is responsive to sequences that have an anomalous frequency distribution.

19. An apparatus as in claim 13, including
a means for examining pathways of genes with respect to gene activation sequences;
a means for extending said pathways using said gene expression information; and
a means for constructing a hypothesized relationship concerning an extension of at least one of said pathways.

20. An apparatus as in claim 13, including
a means for evaluating correlation values with respect to an identified gene or gene sequence so as to determine variations in the behavior of said identified gene or gene sequence; and
a means for confirming said hypothesized relationship in response to applying a statistical technique.

21. Apparatus as in claim 13, said memory including
information associating said hypothesized relationship with a measure of interest by said agent; and
a software comparator coupled to said measure of interest and to a selected threshold.

22. Apparatus as in claim 13, wherein said autonomous software element has access to collateral information other than gene expression values.

23. A memory recording information including instructions, said instructions interpretable by a computing device, said instructions including
an autonomous software element having access to information about a plurality of gene expression values;
a first software element coupled to said information and capable of generating a hypothesized relationship between said gene expression values, said hypothesized relationship having the properties of (1) having a likelihood of being due to chance not exceeding a predetermined value, and (2) satisfying at least one predetermined test indicating that said hypothesized relationship is of potential interest to at least one agent other than said autonomous software element;
a second software element coupled to information about said hypothesized relationship and capable of sending information about said hypothesized relationship to said at least one agent.

24. A memory as in claim 23, including
information about a first set of genes selected in response to said gene expression values;
information about a second set of genes selected in response to data other than said gene expression values;
information about said hypothesized relationship selected in response to applying a statistical technique to said first set and said second set.

25. A memory as in claim 23, wherein generating by the first software element includes
selecting a first set of genes in response to said gene expression values;
selecting a second set of genes in response to data other than said gene expression values;
applying a statistical technique to said first set and said second set; and
confirming said hypothesized relationship in response to applying said statistical technique.

26. A memory as in claim 23, wherein generating by the first software element includes
selecting a set of genes in response to said gene expression values;
comparing the frequencies of the nucleotide sequences upstream from said set of genes to the frequencies of the nucleotide sequences upstream of genes not in said set; and
constructing a hypothesis that is responsive to sequences that have an anomalous frequency distribution.

27. A memory as in claim 23, including
information about examining pathways of genes with respect to gene activation sequences;
information about extending said pathways using said gene expression information; and
information about constructing a hypothesized relationship concerning an extension of said pathways.

28. A memory as in claim 23, wherein the first software element
evaluates correlation values with respect to an identified gene or gene sequence so as to determine variations in the behavior of said identified gene or gene sequence; and
confirms said hypothesized relationship in response to applying a statistical technique.

29. A method including
accessing information about a set of genes and proteins;
generating from said information a hypothesized relationship involving at least one of the following: a set of proteins, SNPs and chemicals pertaining to said information, said hypothesized relationship relative to said information and having a likelihood of being due to chance not exceeding a predetermined value;
retrieving data regarding interests of each agent of a plurality of agents;
identifying at least one agent of the plurality of agents such that the data regarding interests of said at least one agent satisfies at least one predetermined test indicating that said at least one agent has a potential interest in the hypothesized relationship; and
sending information about said hypothesized relationship to said at least one agent.

30. A method as in claim 29, including collecting said information from a plurality of external databases.

31. A method as in claim 29, including collecting said information from at least one external database.

32. A method as in claim 29, wherein the step of identifying includes:
   rating said hypothesized relationship with a measure of interest by said at least one agent; and
   selecting said at least one agent responsive to said measure.

33. A method as in claim 32, wherein the step of selecting includes:
   determining a threshold in said measure of interest; and
   comparing said threshold and said measure of interest.

34. A method as in claim 33, wherein said measure of interest is periodically reevaluated.

35. A method as in claim 33, wherein said data regarding interests includes at least one of: information about interests of said at least one agent, information about published papers, information about researchers, information about relationships between genes.

* * * * *